(12) United States Patent
Stöckl

(10) Patent No.: US 6,926,442 B2
(45) Date of Patent: Aug. 9, 2005

(54) DENTAL X-RAY DEVICE COMPRISING A MOBILE SUPPORT STRUCTURE

(75) Inventor: Klaus Stöckl, Bensheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 0 days.

(21) Appl. No.: 10/834,137

(22) Filed: Apr. 29, 2004

(65) Prior Publication Data

US 2004/0202286 A1 Oct. 14, 2004

Related U.S. Application Data

(63) Continuation of application No. PCT/DE02/04108, filed on Nov. 5, 2002.

(51) Int. Cl.[7] .............................. H05G 1/02; A61B 6/14
(52) U.S. Cl. .......................... 378/197; 378/191; 378/39
(58) Field of Search ................................ 378/197, 191, 378/138–140, 38–40

(56) References Cited

U.S. PATENT DOCUMENTS

| | | | |
|---|---|---|---|
| 2,798,958 A | * 7/1957 | Hudson et al. | 378/39 |
| 3,536,913 A | 10/1970 | Huchel | 250/61.5 |
| 3,636,349 A | * 1/1972 | Faude et al. | 378/40 |
| 3,673,408 A | 6/1972 | Moss | 250/61.5 |
| 4,811,372 A | 3/1989 | Doebert et al. | 378/39 |
| 4,856,044 A | * 8/1989 | Tanguy et al. | 378/198 |
| 5,355,398 A | 10/1994 | Nakano et al. | 378/39 |
| 5,506,879 A | 4/1996 | Mori et al. | 378/39 |

FOREIGN PATENT DOCUMENTS

WO    WO 98/32377    7/1998

* cited by examiner

*Primary Examiner*—David V. Bruce
*Assistant Examiner*—Krystyna Suchecki
(74) *Attorney, Agent, or Firm*—Dykema Gossett PLLC

(57) ABSTRACT

The invention relates to a dental x-ray device comprising a mobile support structure for a system that can be displaced to produce x-ray photographs and also comprising a fixed support structure. The mobile support structure is displaceably mounted on the fixed support structure by one or more bearings. The device is provided with adjustment elements for the displacement of the support structure parallel to the bearing surface, in addition to a drive for carrying out a rotation of the support structure about an axis that is perpendicular to the bearing surface. The bearing elements are configured in such a way that they can be displaced on the bearing surface in every direction parallel to the bearing surface and can carry out a rotation about an axis that is perpendicular to the bearing surface.

20 Claims, 5 Drawing Sheets

DENTAL X-RAY DEVICE COMPRISING A MOBILE SUPPORT STRUCTURE

CROSS REFERENCE TO RELATED APPLICATION

This is a continuation of International Application PCT/DE02/04108, fied Nov. 5, 2002, which designated the U.S. All priorities are claimed.

TECHNICAL FIELD

The invention relates to a dental X-ray device having a supporting structure for an X-ray system adapted to be movable for the purpose of making panoramic images, which should be understood to include panoramic radiograms and transverse tomographic images of the mandibular arch. Furthermore, said X-ray device can also be used for making cephalic images. The movable supporting structure is displaceably mounted on the stationary supporting structure by means of one or more bearings comprising bearing elements secured to at least one supporting structure. At least one supporting structure has a bearing face for the bearing elements. Regulating means are provided for displacing the supporting structure in a direction parallel to said bearing face. Furthermore, a drive is present for effecting rotation of the supporting structure about an axis perpendicular to said bearing face.

BACKGROUND OF THE INVENTION

U.S. Pat. No. 4,811,372 discloses X-ray equipment in which a plate that is mounted via roller bearings on a supporting plate is capable of being moved through a de-fined path, in order to produce a panoramic image (PAN radiogram). The rotational movement of the X-ray unit and image detector is coupled to a disk cam so that during rotation the plate is rotated about a longitudinal axis relatively to the supporting plate.

Another embodiment in U.S. Pat. No. 4,811,372 shows an X-ray device in which swivelling is effected about a stable pivot bearing having a vertical rotation axis and horizontal motion is effected with the aid of sliding guides or stable double-joint arms. A motor for effecting rotational motion drives the system to be moved and consisting of X-ray unit and image detector via a belt about the instant center, and two actuators pro-vide the necessary horizontal movement of the instant center. Rotational motion and translational motion are guided and mounted on bearings in separated elements.

WO 98 32 377 discloses rotating means having a first, stationary plate and a second, floating plate, which is supported on the first plate by at least three balls, and also means for moving said second plate. Each of the opposing surfaces of the plates exhibits as many recesses as there are balls, in which recesses the balls can roll, each ball fitting into both the recess in the stationary plate and the corresponding recess in the floating plate. The path described by the recesses is such that for each position of the floating plate there are three places where the recesses are exactly superposed and in which the respective ball is disposed, in which case the balls roll without sliding when the floating plate is moved. A disadvantage in this case is that only one such path is possible.

SUMMARY OF THE INVENTION

The dental X-ray device of the invention comprises a first, stationary supporting structure and a second supporting structure for a system adapted to be moved for the purpose of making X-ray images, which second supporting structure is displaceably mounted on the first supporting structure by means of one or more bearings. Said bearing comprises bearing elements secured to at least one supporting structure, and at least one supporting structure has a bearing face for the bearing elements, regulating means being provided for effecting a shift of the displaceable supporting structure, and a drive is provided for effecting rotation of the supporting structure about an axis which is perpendicular to the bearing face. The bearing elements are such as to be movable on the bearing face in every direction parallel to the bearing face and as to be rotatable about an axis which is perpendicular to the bearing face.

The advantage of the present invention resides in the combination of the separate bearing and guiding elements such that both rotational and translational movements are possible. Due to the fact that the bearing elements resting on the bearing face have freedom of movement and are thus non-guided, three directions of free movement are made available by a single bearing, ie movement in the horizontal directions to the right or to the left and forwards or backwards and also rotational movement about a vertical axis.

The structure of such a bearing is, compared with known systems using separated elements for rotation and translation, very much simpler and cheaper and still allows for precise and easy movement of the system even when of large mass, particularly when the bearing incorporates rolling elements which substantially roll on the bearing faces instead of sliding thereon.

It will be appreciated that this bearing may be in the form of a plain bearing, if desired, but this requires more powerful actuators on account of the higher frictional resistance involved.

A very exact and reliable system is obtained when the supporting structure to be moved is lightly clamped between two bearings. This is still distinctly less elaborate than is the case with prior systems. Furthermore, the stability and precision of this bearing is better than in prior systems, since in the latter case the bearing clearances and instabilities of the separate bearings and guide means summate.

The dental X-ray device may alternatively be designed such that an X-ray unit is mounted on a first movable supporting structure and the X-ray image detector is mounted on a second movable supporting structure, while both the supporting structure carrying the X-ray unit and the supporting structure carrying the X-ray image detector can be moved relatively to the stationary supporting structure.

The actuators for effecting horizontal movement can act directly on the rotation axis of the system or indirectly act thereon through an element coupled to the supporting structure to be moved, which element follows the instant center but does not follow the rotational movement of the supporting structure.

Other embodiments of the invention are described in the sub-claims.

BRIEF DESCRIPTION OF THE DRAWINGS

An embodiment of the invention is illustrated in the drawings, in which

FIG. 4b is a front view of the schematic construction of FIG. 4a;

FIG. 6b illustrates a ball cage of the bearing of FIG. 6a.

EMBODIMENTS OF THE INVENTION

Figure 1:
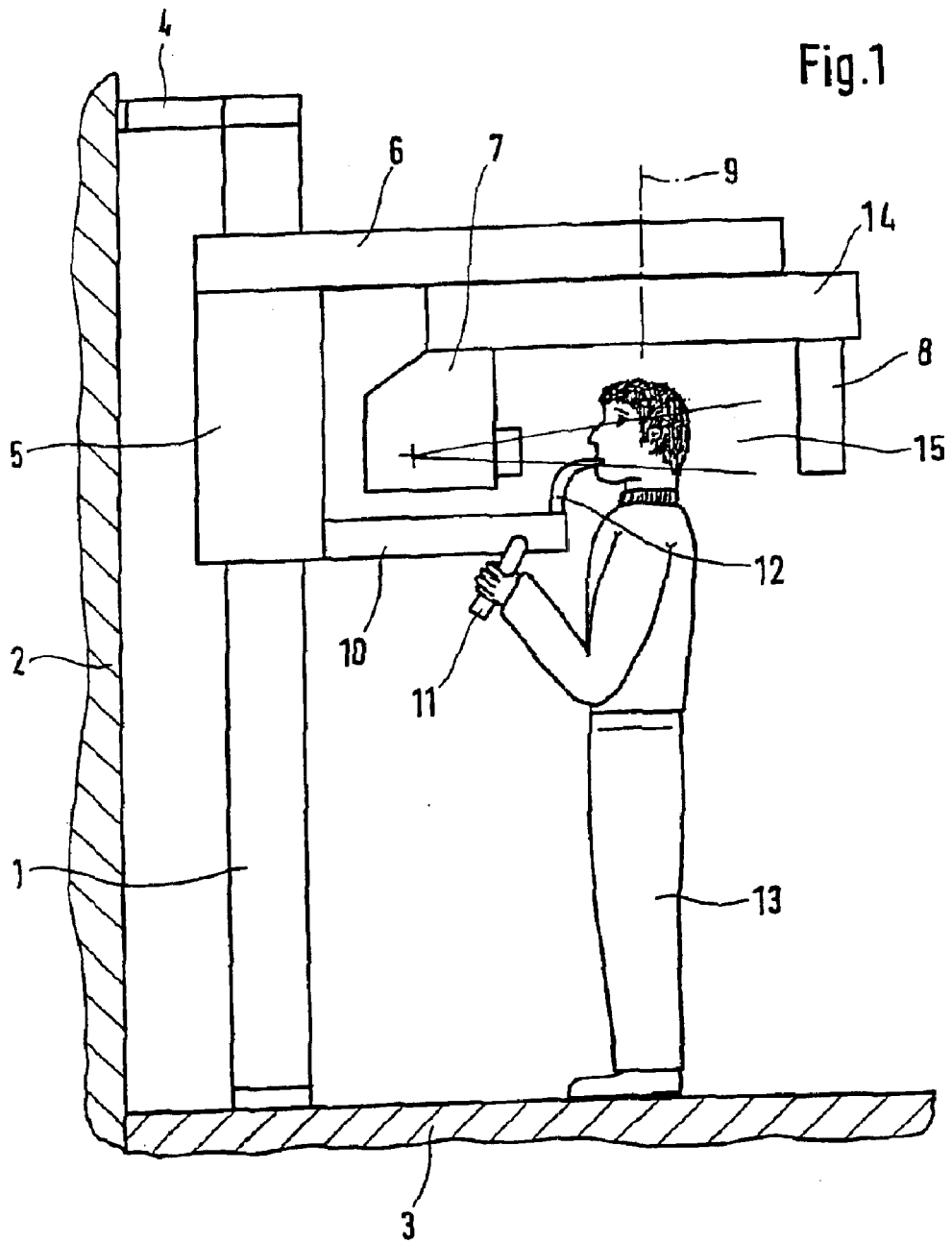
FIG. 1 is a schematic drawing of a dental X-ray device having a movable supporting structure.

The X-ray device illustrated in FIG. 1 has a vertical supporting structure 1 spaced from a wall 2 and mounted at the bottom on a floor 3. Supporting structure 1 is secured at the top to wall 2 by means of a spacer 4. On this vertical supporting structure 1, also referred to as a column, there is mounted a horizontal, vertically adjustable supporting structure 5.

The detailed structure of such an X-ray device is described in detail in EP 0 229 308A1, as is also its mode of operation for making X-ray images. The embodiments disclosed in said application are included in full in this application by reference.

The horizontal supporting structure 5 is provided with a jib or holding arm 6, to which an X-ray unit 7 and an image detector 8 are attached for rotation about a longitudinal axis.

In order to position the patient, the horizontal supporting structure has, in addition, handles 11 and a mouthpiece 12 mounted on a holding arm 10, by means of which a patient 13 retains his position in space while X-ray unit 7 and image detector 8 together rotate about axis 9.

X-ray unit 7 and image detector 8 are interconnected by a supporting structure 14 so that a cone of radiation 15 emanating from X-ray unit 7 impinges on the appropriately oriented image detector.

Figure 2:
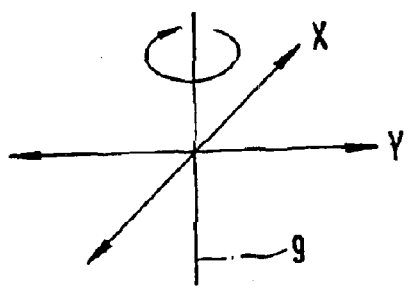
FIG. 2 shows the directions of motion of the movable supporting structure.

The present invention provides a further development of the basic structure, known per se, of an X-ray device for making dental panoramic radiograms as regards the movement of X-ray unit 7 and image detector 8 relatively to horizontal supporting structure 5 such that the directions of motion are possible as indicated in FIG. 2, ie rotation about longitudinal axis 9 and shifts in directions X and Y relatively to the stationary horizontal supporting structure.

Figure 3A:
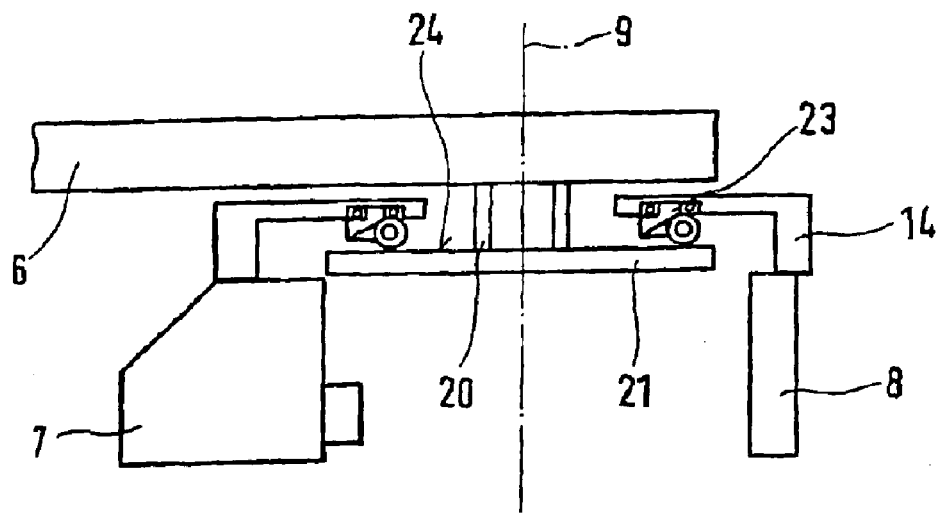
FIG. 3a shows a first bearing enabling the required motion of the supporting structure.

FIG. 3a shows a first arrangement for enabling the required movements. A supporting structure 21 is fixed to holding arm 6 at a distance determined by a spacing bush 22. In the space between stationary supporting structure 21 and holding arm 6 there is situated a second supporting structure 14, which carries X-ray unit 7 and, diametrically opposed thereto, image detector 8, and which is mounted on a bearing face 24 of supporting structure 21 by way of a roller bearing 23 in the form of eccentrically mounted rollers. These "drag" rollers are free for movement on bearing face 24.

The drive for effecting motion and the relevant structural means are described below with reference to FIGS. 4a, 4b.

Figure 3B:
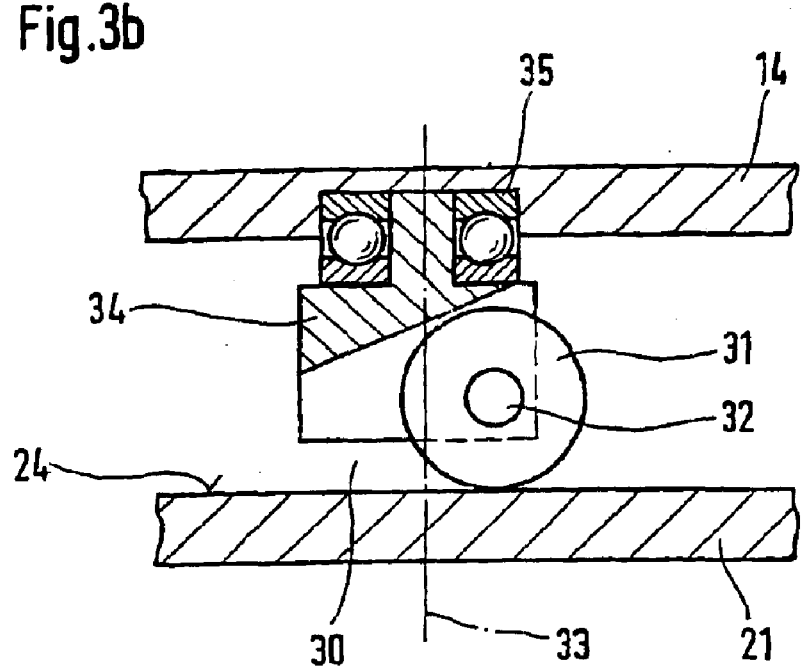
FIG. 3b shows the bearing as a rotatably mounted drag roller in detail.

FIG. 3b is a detail showing a concrete embodiment of bearing 23 in the form of a rotatably mounted drag roller. The drag roller consists of a cylindrical rolling element 31 mounted for rotation on an axle 32, which axle 32 is situated at a distance from a vertical axis 33, which is the axis of rotation of roller housing 34 accommodating rolling element 31 and axle 32. Roller housing 34 is connected to supporting structure 14 via a ball bearing 35. Such drag rollers 30 are known per se and it is well known that by reason of the distance of axle 32 from vertical axis 33 rolling element 31 will always follow the enforced direction of motion. The rolling element can be a ball bearing whose outer ring is reinforced and preferably exhibits a spherical contour. In this case, alignment of roller element 31 by slithering is avoided.

Figure 4A:
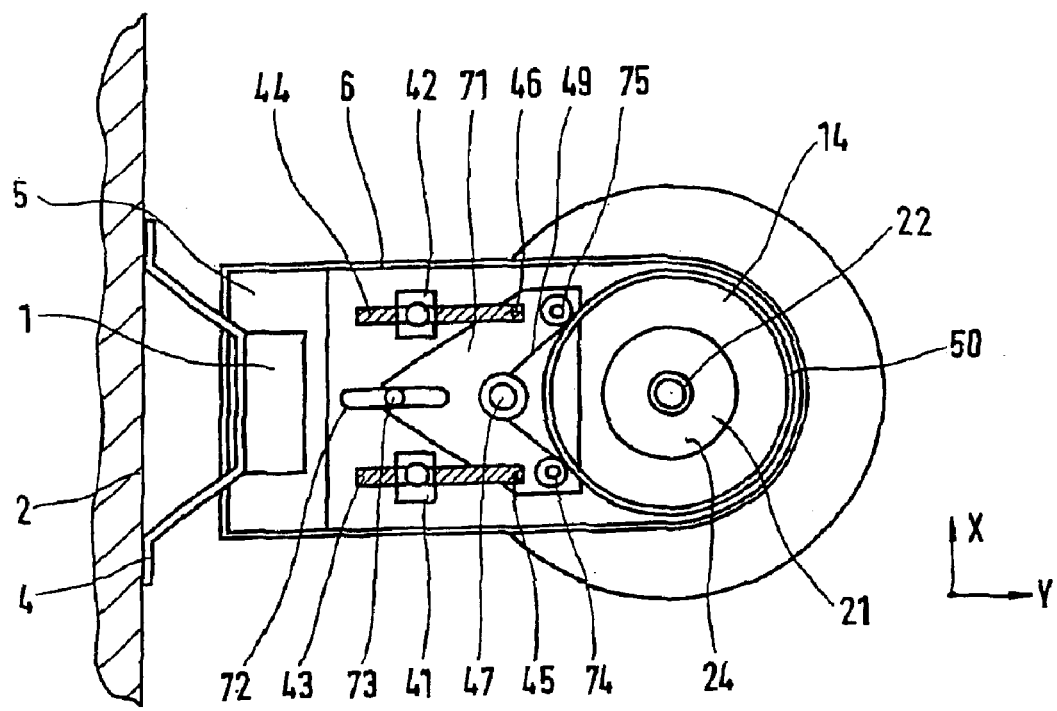
FIG. 4a shows a structure for moving the supporting structure.

FIG. 4a shows a possible arrangement for moving supporting structure 14. Starting from vertical supporting structure 1 secured to wall 2 via spacer 4 and horizontal supporting structure 5 attached thereto, arm 6 is provided with actuators 41, 42, which act via spindles 43, 44 on two pilot pins 45, 46 connected to supporting structure 71. Adjustment of the position of spindles 43, 44, which are rotatably mounted on holding arm 6, by means of actuators 41, 42 causes supporting structure 71 to be shifted in directions X and Y.

In order to prevent uncontrolled swinging of supporting structure 71, another guide is necessary. To this end, supporting structure 71 is in the form of a triangle. Furthermore, a pilot pin 73 is provided for displacement in an oblong hole 72 of supporting structure 6 in direction Y. The pilot pin 73 is guided in supporting structure 6 in such a manner that rotation of supporting structure 71 about a vertical axis extending into the projection plane and translation in direction Y are both possible, whilst no movement in direction X takes place.

A drive 47 causes rotary movement of supporting structure 14, on which the X-ray unit (not shown) and image detector (not shown) are mounted. Rotary motion is effected by way of a belt 49 running around a projection 50 of structure 14. Alternatively, a gear drive might be used. Supporting structure 14 is connected to supporting structure 71 via drive 47 and further pressure rollers 75.

Due to the interrelationship between drive 47, contact rollers 74, 75 and projection 50 on supporting structure 14, supporting structure 14 is guided in the horizontal direction on supporting structure 71 and can at the same time be rotated about a vertical axis 9 or an axis parallel thereto.

When supporting structure 71 is shifted in directions X and Y parallel to bearing face 24 of supporting structure 21 by means of actuators 41, 42, supporting structure 14 follows such movement. Supporting structure 14 is rotatable relatively to supporting structure 71 and is supported during all movements by supporting structure 21 (FIG. 4b).

Figure 4B:
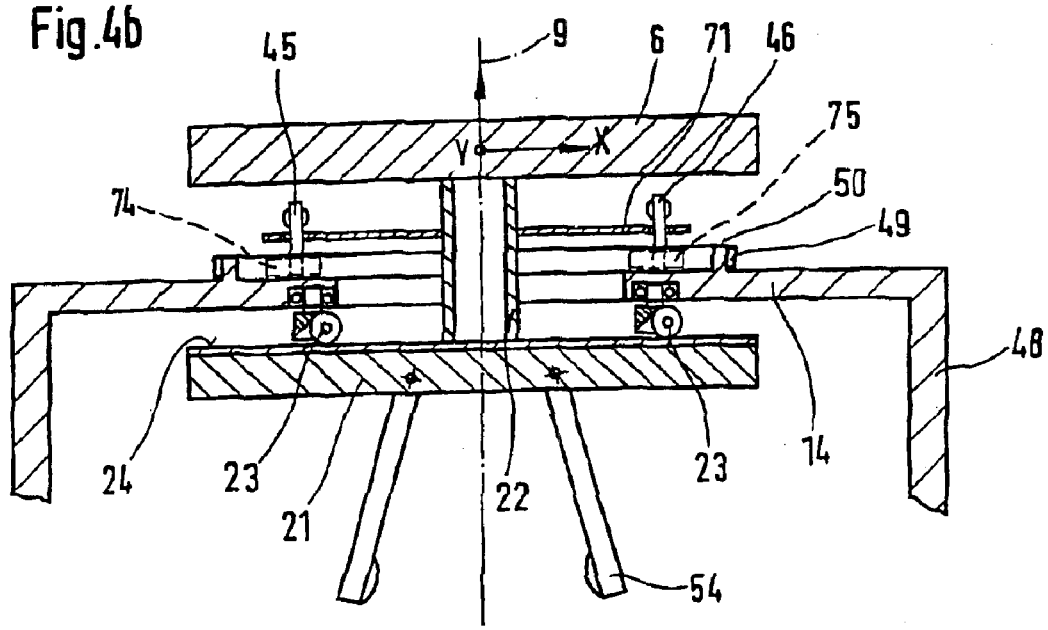

FIG. 4b is a front view of the schematic construction of FIG. 4a. Starting from holding arm 6, to which supporting structure 21 is secured at a distance therefrom by way of a bush 22, supporting structure 14 is shown with its external structure 48. Supporting structure 14 rests on bearing face 24 of supporting structure 21 through bearings 23 and can be moved in directions X and Y parallel to bearing face 24 of supporting structure 21 by means of pilot pins 45, 46 which are connected to supporting structure 71 and which are engaged by the actuators. The bearings can be plain bearings or roller bearings that bear against a wear-resistant bearing face 24. Bearing face 24 is a component which is discrete from supporting structure 21, ie it is in the form of a hardened steel disk on an aluminum support having in itself a soft surface, this being to save weight and expense.

Rotation of supporting structure 14 is effected by projection 50 acting as a belt pulley and driving belt 49 running round the outside of projection 50. Drive 47 can be rigidly mounted on supporting structure 71.

The electromotive adjustment of the system corresponds to the systems disclosed in U.S. Pat. No. 5,355,398 or U.S. Pat. No. 5,506,879, where an X-ray unit and image detector are mounted for rotation about an instant center and the instant center is displaceable in the horizontal plane during rotation.

Figure 5A:
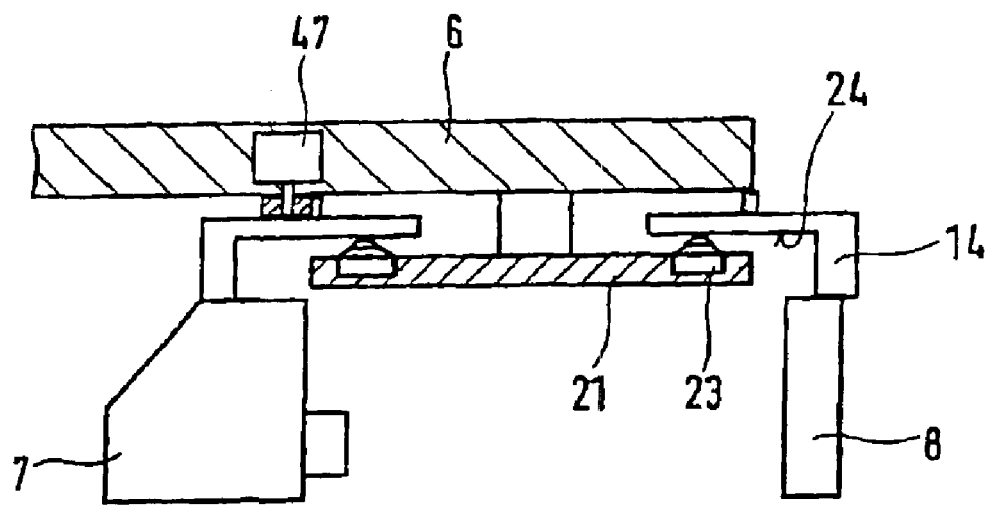
FIG. 5a shows another embodiment of the bearing which is inserted into supporting structure 21, the bearing face being disposed on the supporting structure.

FIG. 5a illustrates another embodiment of bearing 23. Bearing 23 is mounted in supporting structure 21 and bearing face 24 is situated on supporting structure 14. Drive 47 for effecting rotary movement of X-ray unit 7 or image detector 8 is mounted on supporting structure 71 (not shown).

Figure 5B:
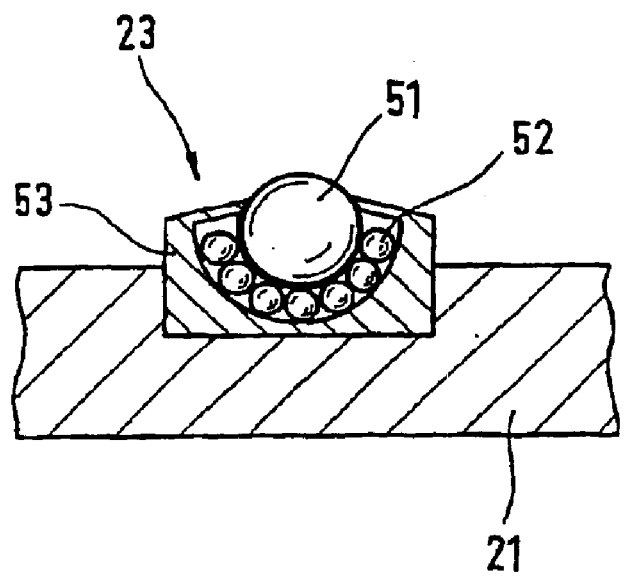
FIG. 5b shows the bearing of FIG. 5a in detail.

FIG. 5b shows bearing 23 in detail. The bearing element that is provided is a ball 51, which is in turn held by small rolling elements in form of balls 52 in a housing 53. Housing 53 is incorporated in supporting structure 21, and fixed in position therein.

Figure 6A:
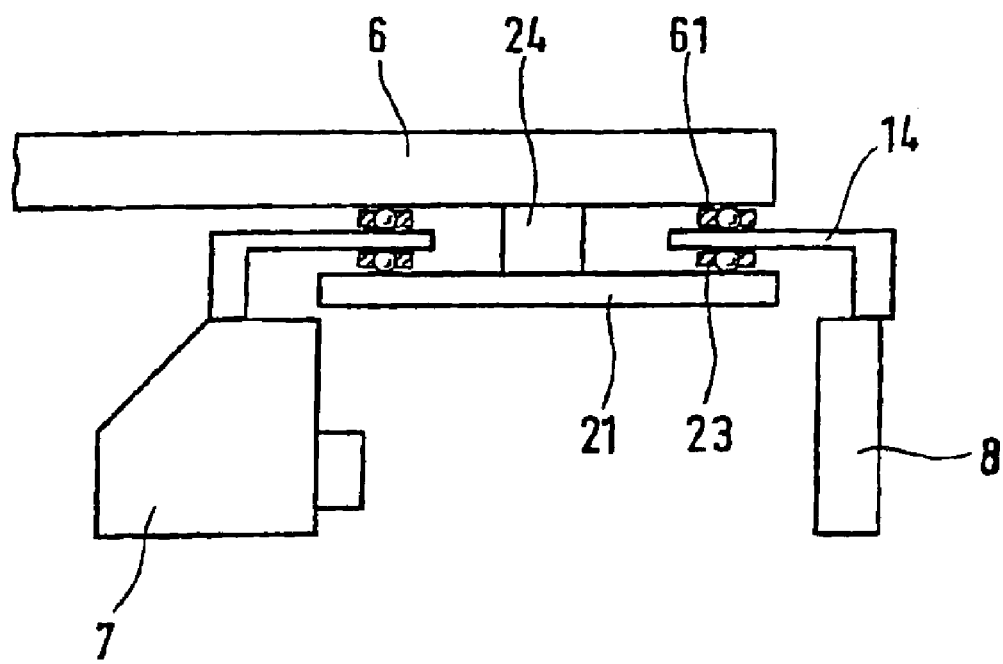
FIG. 6a shows another embodiment of a supporting structure clamped between two bearings.
Figure 6B:
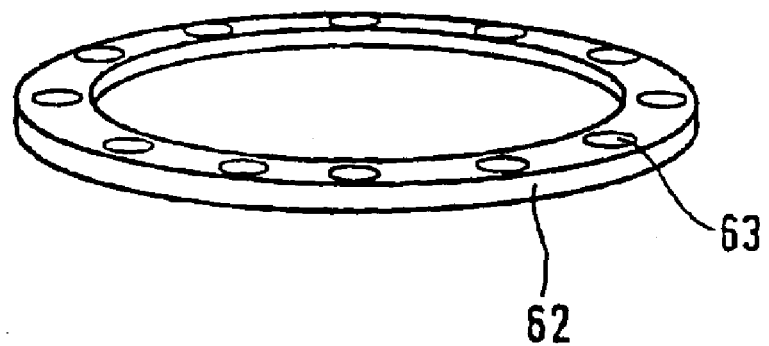

FIGS. 6a and 6b show another embodiment of bearing 23, in which the special feature, apart from the bearing used, is the fact that supporting structure 14 is supported both by supporting structure 21 and by holding arm 6, via bearings 23, 61. Bearings 23, 61 are slightly braced so that supporting structure 14 will still be guided with no backlash when X-ray unit 7 and the image detector and their associated systems have different masses. Tilting of supporting structure 14 is thus avoided.

FIG. 6b shows a cage 62 for rolling elements in the form of balls, which cage has holes 63 for the accommodation of balls.

In this embodiment, supporting structure 21 has a bearing face 24, on which the balls of bearing 23 roll, whilst the balls of bearing 23 also roll against a bearing face of supporting structure 14. Supporting structure 14 is, in addition, provided with another bearing face for the rolling elements of bearing 61 toward holding arm 6, whilst holding arm 6 has a bearing face for the rolling elements of bearing 61. Use is made of a total of two ball cages and four bearing faces as washer disks for the rolling elements.

The bearing can alternatively have only one bearing cage and two spacer disks. In such a case care must be taken to ensure that the center of gravity of the part to be moved is within the polygon defined by the bearings to prevent the system from tilting.

The bias on the bearing is adjusted via connector 24. The provision of bearings on both sides is also possible when use is made of spherical rollers or articulated rollers in accordance with FIGS. 3a, b and FIGS. 5a, b or when plain bearings are used.

Supporting structure 21 is a ring, as is also supporting structure 14, the width of the ring being dimensioned such that the desired range of movement of from 50 to 250 mm in direction X and/or direction Y is made possible.

Head holders can extend from holding arm 6 through joining bush 22 so as to be uninfluenced by the motion of supporting structure 14. The head holders 54 shown in FIG. 4b are, however, directly secured to supporting structure 21.

What is claimed is:

1. A dental X-ray device including at least one of a X-ray emanating unit and a X-ray image detector for producing X-ray images, said device comprising at least one movable supporting structure for a system adapted to be movable for the purpose of making the X-ray images, and having a stationary supporting structure on which said movable supporting structure is displaceably mounted by means of at least one bearing having bearing elements secured to at least one of said movable and stationary supporting structures, at least one of said movable and stationary supporting structures having a bearing face for the bearing elements, regulating means provided for shifting the movable supporting structure in a direction generally parallel to said bearing face, a drive for effecting rotation of said movable supporting structure about an axis generally perpendicular to said bearing face, said bearing elements being movable on the bearing face in any direction generally parallel to said bearing face, and said bearing elements being rotatable about an axis generally perpendicular to said bearing face, wherein the drive effects rotational movement of the movable supporting structure about an instant center, said regulating means including at least two actuators provided for effecting horizontal movement of the instant center independent of the rotational movement, said actuators for effecting said horizontal movement acting directly on a rotation axis of the system or indirectly via a coupled element which follows the center of rotation but does not follow the rotational movement.

2. A dental X-ray device as defined in claim 1, wherein said bearing elements comprise positively guided rolling elements.

3. A dental X-ray device as defined in claim 2, wherein said bearing elements comprise spherical rollers mounted on rolling elements.

4. A dental X-ray device as defined in claim 1, said bearing elements comprise pivotally mounted drag rollers.

5. A dental X-ray device as defined in claim 1, wherein said bearing elements comprise rolling elements, in the form of at least one ball, which are disposed in a cage at spaced intervals.

6. A dental X-ray device as defined in claim 1, said movable supporting structure is displaceably clamped between a pair of bearings, one of said bearings being mounted on said stationary supporting structure, and the other of said bearings being mounted on a holding arm of the x-ray device.

7. A dental X-ray device as defined in claim 1, wherein the bearing elements have a horizontal adjustment range from 50 to 250 mm on said bearing face in all directions.

8. A dental X-ray device as defined in claim 1, wherein a head holder is provided on one of the supporting structures.

9. A dental X-ray device as defined in claim 1, further comprising a second movable supporting structure, the X-ray emanating unit being mounted on the first movable supporting structure and the X-ray image detector being mounted on the second movable supporting structure, said first and second movable supporting structures being movable relative to said stationary supporting structure.

10. A dental X-ray device including at least one of a X-ray emanating unit and a X-ray image detector for producing X-ray images, said device comprising at least one movable supporting structure for a system adapted to be movable for the purpose of making the X-ray images, and having a stationary supporting structure on which said movable supporting structure is displaceably mounted by means of at least one bearing having bearing elements secured to at least one of said movable and stationary supporting structures, said bearing elements comprise pivotally mounted drag rollers, at least one of said movable and stationary supporting structures having a bearing face for the bearing elements, regulating means provided for shifting the movable supporting structure in a direction generally parallel to said bearing face, a drive for effecting rotation of said movable supporting structure about an axis generally perpendicular to said bearing face, said bearing elements being movable on the bearing face in any direction generally parallel to said bearing face, and said bearing elements being rotatable about an axis generally perpendicular to said bearing face.

11. A dental X-ray device as defined in claim 10, wherein the bearing elements have a horizontal adjustment range from 50 to 250 mm on said bearing face in all directions.

12. A dental X-ray device as defined in claim 10, wherein a head holder is provided on one of the supporting structures.

13. A dental X-ray device as defined in claim 10, further comprising a second movable supporting structure, the X-ray emanating unit being mounted on the first movable supporting structure and the X-ray image detector being mounted on the second movable supporting structure, said first and second movable supporting structures being movable relative to said stationary supporting structure.

14. A dental X-ray device as defined in claim 10, wherein the drive effects rotational movement of the movable supporting structure about an instant center, said regulating means including at least two actuators provided for effecting horizontal movement of the instant center, said actuators for effecting said horizontal movement acting directly on a rotation axis of the system or indirectly via a coupled element which follows the center of rotation but does not follow the rotational movement.

15. A dental X-ray device including at least one of a X-ray emanating unit and a X-ray image detector for producing X-ray images, said device comprising at least one movable supporting structure for a system adapted to be movable for the purpose of making the X-ray images, and having a stationary supporting structure on which said movable supporting structure is displaceably mounted by means of at least one bearing having bearing elements secured to at least one of said movable and stationary supporting structures, at least one of said movable and stationary supporting structures having a bearing face for the bearing elements, at least one actuator provided for shifting the movable supporting structure in a direction generally parallel to said bearing face, a drive for effecting rotation of said movable supporting structure about an axis generally perpendicular to said bearing face, said bearing elements being movable on the bearing face in any direction generally parallel to said bearing face, and said bearing elements being rotatable about an axis generally perpendicular to said bearing face, wherein the drive effects rotational movement of the movable supporting structure about an instant center, said actuator effecting horizontal movement of the instant center independent of the rotational movement.

16. A dental X-ray device as defined in claim 15, wherein said bearing elements comprise positively guided rolling elements.

17. A dental X-ray device as defined in claim 15, wherein said bearing elements comprise spherical rollers mounted on rolling elements.

18. A dental X-ray device as defined in claim 15, wherein said bearing elements comprise rolling elements, in the form of at least one ball, which are disposed in a cage at spaced intervals.

19. A dental X-ray device as defined in claim 15, said movable supporting structure is displaceably clamped between a pair of bearings, one of said bearings being mounted on said stationary supporting structure, and the other of said bearings being mounted on a holding arm of the x-ray device.

20. A dental X-ray device as defined in claim 15, further comprising a second movable supporting structure, the X-ray emanating unit being mounted on the first movable supporting structure and the X-ray image detector being mounted on the second movable supporting structure, said first and second movable supporting structures being movable relative to said stationary supporting structure.

* * * * *